United States Patent [19]

Imai et al.

[11] Patent Number: 5,003,121

[45] Date of Patent: Mar. 26, 1991

[54] PRODUCTION OF ALKYL AROMATIC COMPOUNDS

[75] Inventors: Tamotsu Imai, Mt. Prospect; Joseph A. Kocal, Gurnee, both of Ill.

[73] Assignee: UOP

[21] Appl. No.: 399,044

[22] Filed: Aug. 28, 1989

[51] Int. Cl.$^5$ .......................... C07C 2/68; B01J 29/06
[52] U.S. Cl. ...................... 585/467; 502/63; 502/84
[58] Field of Search .................. 502/63, 84; 585/467

[56] References Cited

U.S. PATENT DOCUMENTS

| | | | |
|---|---|---|---|
| 3,849,507 | 11/1974 | Zuesch | 260/671 C |
| 3,962,361 | 6/1976 | Stridde | 260/671 C |
| 3,965,043 | 6/1976 | Stridde | 252/455 R |
| 3,979,331 | 9/1976 | Stridde | 252/441 |
| 4,046,826 | 9/1977 | Stridde | 260/671 C |
| 4,075,126 | 2/1978 | Stridde | 252/455 R |
| 4,499,319 | 2/1985 | Ballentine et al. | 585/467 |
| 4,510,257 | 4/1985 | Lewis et al. | 502/84 |
| 4,605,806 | 8/1986 | Ballantine et al. | 585/467 |
| 4,637,992 | 1/1987 | Lewis et al. | 502/84 |
| 4,749,808 | 6/1988 | Ballentine et al. | 568/247 |

*Primary Examiner*—H. M. S. Sneed
*Assistant Examiner*—J. Saba

[57] ABSTRACT

Alkyl aromatic compounds may be prepared by reacting an aromatic compound with an alkylating agent such as an olefin in the presence of an alkylation catalyst. The alkylation catalyst of the present invention comprises a composite which has been prepared by coextruding a clay component and at least one multivalent metal component in which the metal is selected from the group consisting of Groups IIIA, IIIB and IVB of the Periodic Table, followed by drying the resultant extrudate and calcination thereof. By utilizing a catalyst which has been prepared by this method in an alkylation reaction it is possible to obtain an improved alkylate selectivity.

24 Claims, No Drawings

PRODUCTION OF ALKYL AROMATIC COMPOUNDS

BACKGROUND OF THE INVENTION

Alkyl aromatic compounds form important chemicals which may be utilized as intermediates in many industrial applications as, for example, polymeric material, plasticizers, detergents, etc. Heretofore, the production of alkyl aromatic compounds has been effected by alkylating an aromatic compound with an alkylating agent in the presence of acidic catalysts. These acidic catalysts include sulfuric acid and hydrofluoric acid due to the relatively good activity for the purpose intended. However, the use of these liquid acids such as sulfuric acid or hydrofluoric acid has inherently some drawbacks or shortcomings. The acids hereinbefore named are extremely corrosive in nature, thus requiring special handling and equipment due to the dangerous nature thereof. In addition, the use of these acids might also involve some environmentally hazardous problems which are attendant thereto. Therefore, it would be preferable to utilize a safer and more simple catalyst, preferentially in solid state, in a fixed bed reactor to produce the desired compounds. The use of a simpler process would result in less capital investment and therefore enable the producer to provide a less expensive product.

In view of this we have now discovered that a solid alkylation catalyst may be employed to effect the desired alkylation to obtain a production which is equal in quality to those products obtained when utilizing liquid acidic catalyst while also improving the activity of the catalyst as well as the selectivity of the product.

Prior patents have described the use of solid catalysts comprising clays which contain a metallic component. For example, U.S. Pat. No. 4,499,319 discloses a cation-exchanged layered clay in which a layered clay having a lamellar structure is ion-exchanged with a metallic cation. The catalyst is then activated by heating in air at a temperature in the range of from about 80° to 200° C. The catalyst may be used to alkylate aromatic compounds with an alkylating agent containing less than about 6 carbon atoms. U.S. Pat. No. 4,749,808 also uses a metal cation-exchanged clay to produce an ester by reacting an olefin or an olefin oxide with a carboxylic acid. U.S. Pat. Nos. 3,849,507 and 4,605,806 both utilize hydrogen ion-exchanged layered clays as catalysts for producing esters in a manner similar to that set forth in the above-enumerated patents.

U.S. Pat. No. 3,962,361 utilizes an ion-exchanged synthetic saponite clay for acid catalyzed reactions in which the clay is ion-exchanged with a metal cation and activated by heating to a temperature less than 200° C. Likewise, U.S. Pat. No. 3,965,043 similar discloses an ion-exchanged natural clay for use in alkylating aromatic hydrocarbons similar to the prior named patent. Other U.S. patents which disclose alkylating catalysts which are solid in nature include U.S. Pat. Nos. 3,979,331, 4,046,826 and 4,075,126. These patents disclose alkylation of aromatic compounds with a synthetic clay which has been cation-exchanged and activated.

It is to be noted that many of the prior patents which have been discussed employ clays which have been subjected to a process whereby a metal cation is exchanged for the hydrogen ions normally present in the clay. The catalyst of the present invention which we have discovered comprises a clay in which a metal cation is impregnated throughout the clay rather than having the ion exchanged thereon. This catalyst will possess excellent characteristics with regard to the activity of the catalyst as well as to the selectivity of the product which is obtained by the reaction.

BRIEF SUMMARY OF THE INVENTION

This invention relates to a process for producing alkyl aromatic compounds as well as to a catalyst which may be used to effect the desired reaction. As was previously set forth, alkyl aromatic compounds may be utilized in many and varied industrial applications. For example, one of the major problems which is prevalent in population centers throughout the world is the disposal of sewage containing detergents dissolved therein. Such disposal problems are especially trying in instances where the detergents comprise branched chain alkylaryl compounds. These branched chain detergents produce stable foams in either hard or soft waters in such large quantities that the foam tends to clog sewage treatment facilities and destroy the bacteria which are necessary for proper sewage treatment. These unwanted foams or suds are found in many rivers, streams, lakes, etc. which provide a water supply for the aforesaid population centers. As hereinbefore set forth, the presence of these unwanted foams or suds is due in many instances to the use of detergents which are non-biodegradable in nature and which will not break down due to bacterial action thereon. This non-biodegradable nature of the detergents is due to the fact that the alkyl side chain of the molecule is, in many instances, highly branched in nature and therefore is not readily attacked by organisms which would ordinarily destroy the molecules. In contradistinction to this, the presence of straight chain alkyl substituents on the ring will permit bacteria to act upon the alkyl chain and destroy the detergents, thereby minimizing the formation of foams or suds which will then not build up on the surface of the water or throughout the water.

By utilizing the catalytic composition of matter of the present invention it is possible to obtain straight chain alkylaryl detergents due to the excellent selectivity characteristics of the catalyst, especially with regard to alpha-olefins to obtain the desired alkyl aromatic product. As will hereinafter be shown in greater detail when utilizing the particular catalytic composition of matter of the present invention it is possible to effect an alkylation process in which the activity of the catalyst will be maintained for a relatively lengthy period of time as well as obtaining a selective product from the reaction.

It is therefore an object of this invention to provide a novel catalytic composition of matter which may be used to effect an alkylation of aromatic compounds.

A further object of this invention is to provide a process for preparing such a catalytic composition and in addition to provide the necessary process for producing an alkyl aromatic compound.

In one aspect an embodiment of this invention comprises a catalytic composition of matter prepared by coextruding a clay component and at least one multivalent metal component selected from the group consisting of Group IIIA of the Periodic Table, Group IIIB of the Periodic Table and Group IVB of the Periodic Table, drying the resultant extrudate, calcining said extrudate at calcination conditions and recovering the calcined extrudate comprising a catalytic composition of matter.

A further embodiment of this invention resides in a process for the production of a catalytic composition of matter which comprises adding an aqueous solution containing at least 1 multi-valent metal selected from the group consisting of Group IIIA of the Periodic Table, Group IIIB of the Periodic Table and Group IVB of the Periodic Table to a dough of clay, extruding the resultant mixture, drying said mixture, calcining said mixture at calcination conditions, and recovering the resultant catalytic composition.

Yet another embodiment of this invention is found in a process for the production of an alkyl aromatic compound which comprises reacting an aromatic compound with an alkylating agent selected from the group consisting of olefins, alkyl halides and alkyl alcohols at alkylation conditions in the presence of a catalytic composition of matter, prepared by coextruding a clay component and at least one multi-valent metal component selected from the group consisting of Group IIIA of the Periodic Table, Group IIIB of the Periodic Table and Group IVB of the Periodic Table, drying the resultant extrudate, calcining said extrudate at calcination conditions and recovering the calcined extrudate comprising a catalytic composition of matter, in an alkylation zone, and recovering the resultant alkyl aromatic compound.

A specific embodiment of this invention resides in a catalytic composition of matter prepared by coextruding a mixture of montmorillonite and cerium, drying the resultant extrudate, calcining said extrudate at a temperature in the range of from about 300° to about 800° C. and recovering the resultant catalytic composition of matter.

Another specific embodiment of this invention resides in a process for the production of a catalytic composition of matter which comprises adding an aqueous solution of cerium to clay, extruding the resultant doughy mixture, drying said mixture, calcining said mixture at a temperature in the range of from about 300° to about 800° C. and recovering the resultant catalytic composite.

Yet another specific embodiment of this invention is found in a process for the production of an aromatic compound which comprises reacting benzene with an alkylating agent comprising a mixture of olefins containing from 9 to about 15 carbon atoms at a temperature in the range of from about 80° to about 450° C. and a pressure in the range of from about 500 to about 2,000 pounds per square inch gauge in the presence of a catalyst which has been prepared by coextruding a mixture of montmorillonite and cerium, drying the resultant extrudate, calcining said extrudate and recovering the calcined extrudate, in an alkylation zone and recovering the resultant alkylated benzene.

Other objects and embodiments will be found in the following detailed description of the invention.

DETAILED DESCRIPTION OF THE INVENTION

As hereinbefore set forth the present invention is concerned with a catalyst which is useful in the alkylation of aromatic compounds and particularly to catalytic composite which will possess excellent characteristics with respect to the activity and selectivity of the alkyl aromatic compound which is produced during the reaction. In addition, the invention also is concerned with a process for preparing an alkyl aromatic compound utilizing the catalyst hereinafter described in greater detail.

The catalytic composite of the present invention comprises a mixture of clay and at least one multi-valent metal. The mixture is extruded, dried and calcined to form the desired catalyst.

The multi-valent metals which are utilized to impregnate a clay of the type hereinafter set forth will comprise in particular those metals found in Groups IIIA and IIIB of the Periodic Table including aluminum, gallium, indium, thallium, scandium, yttrium, lanthanum, as well as cerium and mixtures of rare earth metals and Group IVB of the Periodic Table including titanium, zirconium, and hafnium. The aforementioned metals are admixed with a clay which may be naturally occurring and which will include such clays as bentonite, montmorillonite, smectite, kaolin, attapulgus, hectorite, chlorite, beidellite, etc. In the preferred embodiment of the invention the multi-valent metal or mixture of multi-valent metals will be present in the catalytic composite in an amount in the range of from about 0.5 to about 10% by weight of the catalytic composite.

The catalytic composite of the present invention may be prepared by admixing an aqueous solution containing at least one multi-valent metal with a clay of the type hereinbefore set forth in greater detail to form an extrudable doughy mass. Some representative examples of water soluble salts include, aluminum chloride, aluminum nitrate, aluminum iodide, aluminum chlorate, gallium chloride, gallium iodide, gallium nitrate, gallium sulfate, indium bromide, indium chloride, indium iodide, indium nitrate, indium sulfate, titanium chloride, titanium iodide, titanium nitrate, titanium oxillate, zirconium chloride, zirconium iodide, zirconium nitrate, zirconium oxiiodide, lanthanum bromide, lanthanum chloride, scandium nitrate, scandium chloride, yttrium bromide, yttrium chloride, yttrium iodide, cerous bromide, cerous nitrate, etc. or mixtures thereof.

The mass is extruded to provide a predetermined shaped extrudate which may be in the forms of pellets, spheres, etc. which is then subjected to an evaporation or drying step in which the aqueous portion of the soluble salt is removed, said step being effected at temperatures ranging from ambient (20°-25° C.) to about 100° C. Following the drying step the impregnated clay is then subjected to a calcination step in which the composite is heated to a temperature in the range of from about 300° up to about 800° C. for a period of time which may range from about 1 to about 24 hours. The calcination of the composite may be effected in an air atmosphere or in an air atmosphere which contains from 1 to about 20% steam.

As an alternative to this method the clay may be admixed with from about 5% to about 50% by weight of a binder which, in the preferred embodiment of the invention, comprises an inorganic oxide such as alumina. This mixture is then treated with the aqueous solution containing at least 1 multi-valent metal to form an extrudable mass which is then extruded through an appropriate die and thereafter subjected to drying and calcination steps similar to those set forth in the above paragraphs. By extruding a quasi-impregnated clay the impregnation of the clay begins with the admixing of the aqueous solution of the clay and continues during extrusion to be finally completed after drying and calcination. It is possible to prepare the desired alkylation catalyst in a more economical manner. The process is rendered more economical inasmuch as when preparing the catalyst in a conventional manner such as calcining a clay followed by impregnation, drying and calcination it is possible to eliminate one calcination step and a separate impregnation step. Therefore less capitol equipment will be involved with the resulting savings in cost of preparing the desired catalyst.

The alkylation of aromatic compounds utilizing the catalytic composite of the present invention may be effected in any suitable manner utilizing either a batch type or a continuous type operation. The aromatic compounds which are treated with an alkylating agent may comprise either monocyclic or polycyclic compounds. In addition, the aromatic compounds may also contain substituents on the ring, examples of the aromatic compounds including benzene, toluene, o-xylene, m-xylene, p-xylene, ethylbenzene, naphthalene, isomeric methyl naphthalenes, isomeric ethyl naphthalenes, anthracene, chrysene, pyrene, etc. Alkylating agents which are utilized as the second component in the process will comprise olefins containing from 2 to about 20 carbon atoms, alkyl halides, alcohols, etc. Some specific examples of these alkylating agents will include ethylene, propylene, the isomeric butenes, pentenes, hexenes, heptenes, octenes, nonenes, decenes, undecenes, dodecenes, tridecenes, tetradecenes, pentadecenes, hexadecenes, heptadecenes, octadecenes, nonadecenes, eicosenes, etc., methyl chloride, ethyl chloride, propyl chloride, butyl chloride, hexyl chloride, octyl chloride, decyl chloride, dodecyl chloride, tetradecyl chloride, methyl bromide, ethyl bromide, propyl bromide, butyl bromide, heptyl bromide, nonyl bromide, undecyl bromide, etc., methyl alcohol, ethyl alcohol, propyl alcohol, isopropyl alcohol, n-butyl alcohol, sec-butyl alcohol, etc. In addition, it is also contemplated that mixtures of olefins may also be employed as alkylating agents. It is to be understood that the aforementioned aromatic compounds and alkylating agents are only representative of the type of compounds which may be employed as reactants in the alkylation process and that the present invention is not necessarily limited to these compounds.

The alkylation reaction may be effected in a batch type operation by placing the aromatic compound and the alkylating agent in an appropriate apparatus such as an autoclave of the rotating or mixing type along with the catalytic composite. In the preferred embodiment of the invention the alkyl aromatic compound is present in the reaction mixture in an excess of alkylating agent, preferably in a range of from about 2:1 to about 20:1 moles of aromatic compound per mole of alkylating agent. The reactor is sealed and heated to the desired operating temperature which may be in a range of from about 8° to about 200° C. In addition, in order to preferably effect the reaction in a liquid phase pressure is added to maintain an operating pressure in the range of from about 200 to about 1,000 pounds per square inch gauge. The operating pressure which is employed may be provided for by the introduction of an inert gas such as nitrogen, helium, argon, etc. when the alkylating agent is in liquid form. Conversely if the alkylating agent which is employed is in gaseous form a portion of the operating pressure may be afforded by the autogenous pressure of the gaseous alkylating agent while the remainder is afforded by the presence of an inert gas. Upon completion of the reaction time which may range from about 0.5 up to about 4 hours or more in duration, heating is discontinued and after the reactor and contents thereof have returned to room temperature excess pressure is vented, the autoclave is opened and the reaction mixture is recovered therefrom. The desired alkyl aromatic compound may then be separated from any unreacted starting materials by conventional means such as fractional distillation and recovered.

When the alkylation reaction of the present invention is effected in a continuous manner a quantity of the catalytic composite is placed in a reactor which may be tubular in configuration. The reactor is heated to the desired operating temperature and brought up to the desired operating pressure, following which the reactants comprising the aromatic compound and the alkylating agent are continuously passed over the catalyst bed at a predetermined liquid hourly space velocity. After passage through the catalyst bed for a predetermined period of time the reactor effluent is continuously withdrawn and subjected to conventional separation means whereby the desired alkyl aromatic product is separated and recovered while any unreacted starting materials may be recycled to the reactor to form a portion of the feedstock.

Inasmuch as the catalytic composite of the present invention is solid in nature, various types of continuous operation may be employed. For example, the catalyst may be maintained in the reactor as a fixed bed while the aromatic compound and alkylating agent are passed through the bed in either an upward or downward flow. Alternatively, a moving bed type of operation may be employed in which the catalyst bed and the reactants are passed through the reactor either concurrently or countercurrently to each other. Likewise, a slurry type operation may be employed in which the catalyst is carried into the reactor as a slurry in one or both of the reactants.

The following examples are given for purposes of illustrating the novel catalytic compositions of matter and the process of the present invention. However, it is to be understood that these examples are given merely for purposes of illustration and that the present invention is not necessarily limited thereto.

EXAMPLE I

One catalyst of the present invention was prepared by admixing 750 g of a clay known in the trade as Filtrol 113 which is a Montmorillonite type of clay with an aqueous solution of cerium nitrate sufficient to afford 2.8% of cerium on the finished catalyst. The resulting paste or dough was extruded through a die to form 1/32 inch extrudates. After drying at a temperature of 90° C. the extrudate was calcined in an air atmosphere containing 10% steam for a period of 2 hours at 600° C. This catalyst was labeled A.

EXAMPLE II

In a manner similar to that set forth in Example I above a catalyst was prepared by forming a mixture which contained 80% of a clay known in the trade as Filtrol 13 with 20% of alumina. The admixture was treated with an aqueous solution of cerium nitrate sufficient to afford a 3% by weight amount of cerium on the finished catalyst. The resulting dough was extruded through a die to provide 1/32 inch extrudates. The extrudates were dried and calcined in an air atmosphere containing 10% steam for two hours at a temperature of 600° C. This catalyst was labeled B.

EXAMPLE III

A third catalyst was formed by extruding a doughy mass of Filtrol 113 to form 1/32 inch extrudates which were dried and calcined in an air atmosphere containing 10% steam for a period of 2 hours at 600° C., said catalyst being designated as catalyst C.

EXAMPLE IV

A fourth catalyst was prepared by forming a doughy paste comprising 80% Filtrol 13 and 20% alumina. The paste was extruded through a die to form 1/32 inch extrudates which were then calcined in an air atmosphere containing 10% steam for a period of 2 hours at 600° C. This catalyst was designated as D.

EXAMPLE V

The four catalysts were utilized in an alkylation reaction by placing 25 cc of each catalyst in tubular stainless steel reactors having an inside diameter of ½ inch. A feedstock comprising a mixture of benzene and an alkylating agent consisting of a mixture of olefins containing from 10 to 14 carbon atoms in a benzene/olefin ratio of 8:1 was charged to the reactor at a Liquid Hourly Space Velocity of 2.5 hrs.$^{-1}$. The reactor was maintained at a temperature of 150° C. under a pressure of 500 pounds per square inch gauge. The product which was recovered from the reactor was analyzed to determine the percent of olefin conversion, the percent of detergent alkylate selectivity and the percent of linearity. The results of these analyses are set forth in the table below.

|  | A | B | C | D |
|---|---|---|---|---|
| Olefin Conversion % | 99+ | 99+ | 99+ | 99+ |
| Detergent Alkylate Selectivity Weight Percent | 85 | 91.5 | 79 | 80.6 |
| Percent linearity | 93 | 93.6 | 93 | 93.8 |

It will be noted from the above table that the detergent alkylate selectivity which may be defined as the weight of total monoalkylbenzenes divided by the total weight of all products including dialkyl benzenes, olefinic oligomers and monoalkyl benzenes is greater in all instances where the catalyst contains a multi-valent metal as compared to the catalysts which do not contain the metal. This therefore clearly indicates that the presence of a multi-valent metal with the clay results in the obtention of a greater amount of a desired product comprising a monoalkyl benzene which may then be used as an intermediate in the preparation of biodegradable detergents.

We claim as our invention:

1. A catalytic composition of matter prepared by coextruding a clay component and at least one multi-valent metal component selected from the group consisting of Group IIIA of the Periodic Table, Group IIIB of the Periodic Table, and Group IVB of the Periodic Table, drying the resultant extrudate, calcining said extrudate at calcination conditions and recovering the calcined extrudate comprising a catalytic composition of matter.

2. The catalytic composition of claim 1 in which said multi-valent metal or mixture of multi-valent metals is present in an amount in the range of from about 0.5% to about 10% by weight of said composition.

3. The catalytic composition of claim 1 in which said multi-valent metal is aluminum.

4. The catalytic composition of claim 1 in which said multi-valent metal is lanthanum.

5. The catalytic composition of claim 1 in which said multi-valent metal is cerium.

6. The catalytic composition of claim 1 in which said multi-valent metal is a mixture of aluminum and cerium.

7. The catalytic composition of claim 1 in which said clay is montmorillonite.

8. The catalytic composition of claim 1 in which said clay is kaolin.

9. The catalytic composition of claim 1 in which said clay is bentonite.

10. The catalytic composition of claim 1 in which said catalytic composition contains from about 5% to about 50% by weight of a binder.

11. The catalytic composition as set forth in claim 10 in which said binder is alumina.

12. A process for the production of an alkyl aromatic compound which comprises reacting an aromatic compound with an alkylating agent selected from the group consisting of olefins, alkyl halides and alkyl alcohols at alkylation conditions in the presence of a catalytic composition of matter, prepared by coextruding a clay component and at least one multi-valent metal component selected from the group consisting of Group IIIA of the Periodic Table, Group IIIB of the Periodic Table, and Group IVB of the Periodic Table, drying the resultant extrudate, calcining said extrudate at calcination conditions and recovering the calcined extrudate comprising a catalytic composition of matter, in an alkylation zone, and recovering the resultant alkyl aromatic compound.

13. The process of claim 12 in which said alkylation conditions include a temperature in the range of from about 80° to about 450° C. and a pressure in the range of from about 50 to about 2,000 pounds per square inch gauge.

14. The process of claim 12 in which said alkylation agent contains from 1 to about 20 carbon atoms.

15. The process of claim 12 in which said aromatic compound and said alkylating agent is present in said alkylation zone in a mole ratio of aromatic compounds to alkylating agent in a range of from about 2:1 to about 20:1.

16. The process of claim 12 in which said aromatic compound is benzene.

17. The process of claim 12 in which said aromatic compound is naphthalene.

18. The process of claim 12 in which said alkylating agent comprises an olefinic hydrocarbon mixture containing from about 9 to about 15 carbon atoms.

19. The process of claim 12 in which said catalytic composition contains from about 5% to about 50% by weight of a binder.

20. The process of claim 19 in which said binder is alumina.

21. The process of claim 12 in which said clay is montmorillonite.

22. The process of claim 12 in which said clay is kaolin.

23. The process of claim 12 in which said multi-valent metal is aluminum.

24. The process of claim 12 in which said multi-valent metal is cerium.

* * * * *